United States Patent
Liang et al.

(10) Patent No.: US 9,251,606 B2
(45) Date of Patent: Feb. 2, 2016

(54) COMPUTERIZED IMAGE RECONSTRUCTION METHOD AND APPARATUS

(71) Applicant: The Research Foundation of The State University of New York, Albany, NY (US)

(72) Inventors: Zhengrong Liang, Stony Brook, NY (US); Jianhua Ma, Stony Brook, NY (US); Yan Liu, Stony Brook, NY (US)

(73) Assignee: The Research Foundation for The State University of New York, Albany, NY (US)

(*) Notice: Subject to any disclaimer, the term of this patent is extended or adjusted under 35 U.S.C. 154(b) by 0 days.

(21) Appl. No.: 14/376,177

(22) PCT Filed: Feb. 1, 2013

(86) PCT No.: PCT/US2013/024423
§ 371 (c)(1),
(2) Date: Aug. 1, 2014

(87) PCT Pub. No.: WO2013/116709
PCT Pub. Date: Aug. 8, 2013

(65) Prior Publication Data
US 2015/0030227 A1 Jan. 29, 2015

Related U.S. Application Data

(60) Provisional application No. 61/593,634, filed on Feb. 1, 2012.

(51) Int. Cl.
*G06K 9/00* (2006.01)
*G06T 11/00* (2006.01)
*A61B 6/03* (2006.01)

(52) U.S. Cl.
CPC .............. *G06T 11/005* (2013.01); *A61B 6/032* (2013.01); *G06T 11/006* (2013.01);
(Continued)

(58) Field of Classification Search
USPC ......................................................... 382/131
See application file for complete search history.

(56) References Cited

U.S. PATENT DOCUMENTS

2003/0076988 A1* 4/2003 Liang ..................... G06T 5/10
382/131
2003/0156684 A1* 8/2003 Fessler ................... A61B 6/032
378/210

(Continued)

OTHER PUBLICATIONS

PCT/ISA/237 Written Opinion issued on PCT/US2013/024423 (pp. 3).

(Continued)

*Primary Examiner* — John Strege
(74) *Attorney, Agent, or Firm* — The Farrell Law Firm, P.C.

(57) ABSTRACT

Provided herein is a computerized image reconstruction apparatus and method that includes recording projection path information and energy loss information of a plurality of particles traversing an object being imaged and determining an estimated image of the object based on the projection path information and the energy loss information sampled into a projection format. The estimated image includes an active volume defined by an enclosure border. Cost function minimization uses an Adaptive-weighted Total Variation cost function, a Penalized Weighted Least-Squares cost function, or an Alpha-Divergence cost function to update the estimated image. An iterative updating algorithm corresponding to the cost function updates the estimated image and produces a final image based on the estimated image according to a predetermined threshold.

13 Claims, 6 Drawing Sheets

(52) U.S. Cl.
CPC ............... *G06T 2207/10081* (2013.01); *G06T 2207/10124* (2013.01); *G06T 2207/30096* (2013.01); *G06T 2211/424* (2013.01)

(56) References Cited

U.S. PATENT DOCUMENTS

| | | |
|---|---|---|
| 2005/0105693 A1 | 5/2005 | Zhao et al. |
| 2006/0104410 A1 | 5/2006 | Sauer et al. |
| 2007/0031337 A1 | 2/2007 | Schulte |
| 2007/0297656 A1* | 12/2007 | DeMan ................ G01N 23/046 382/128 |
| 2008/0187091 A1* | 8/2008 | Basu .................... G01N 23/046 378/5 |
| 2009/0225932 A1* | 9/2009 | Zhu ........................ A61B 6/032 378/7 |
| 2011/0044546 A1 | 2/2011 | Pan et al. |
| 2011/0220794 A1 | 9/2011 | Censor et al. |
| 2011/0262054 A1* | 10/2011 | Benson ................ G01N 23/046 382/275 |
| 2012/0155728 A1* | 6/2012 | DeMan .................. G06T 11/006 382/131 |

OTHER PUBLICATIONS

PCT/ISA/210 Search Report issed on PCT/US2013/024423 (pp. 3).

* cited by examiner

COMPUTERIZED IMAGE RECONSTRUCTION METHOD AND APPARATUS

PRIORITY

This application claims priority to U.S. Provisional Application No. 61/593,634, filed with the U.S. Patent and Trademark Office on Feb. 1, 2012, the entire content of which is incorporated herein by reference.

BACKGROUND OF THE INVENTION

1. Field of the Invention

The present invention generally relates to computerized image reconstruction and, more particularly, to image reconstruction from projected data along curved paths of proton particles through an object being imaged.

2. Description of the Related Art

Computed tomographic image reconstruction has typically focused on X-rays or photons that pass through the body in a straight line. Any path deviation from an original direction is considered as the path of scattered particles and may be ignored. Such imaging modalities, such as X-ray Computed Tomography (xCT) or simple CT, Single-Photon Emission Computed Tomography (SPECT) and Positron Emission Tomography (PET), provide high energy X-rays or Gamma-rays that travel along a straight line path inside the body. The various image reconstruction methodologies and algorithms developed and applied to these imaging modalites generate satisfactory image quality for diagnosis and other medical applications.

However, travel paths of heavy particles, such as proton, muon, neutron, carbon, alpha particle, do not follow a straight line within the body, and present image reconstruction difficulties for proton Computed Tomography (pCT).

Clinical applications of pCT and proton beam treatments in medicine provide improved radiation therapy due to the distinct advantages of proton beams compared to other radiation therapy options, such as X-rays, electron beams. Proton beams deliver radiation energy in a precise manner and leave normal tissues around targeted diseased tissue, such as a tumor, mostly unharmed or undamaged. Thus, there is a growing demand for efficient, low-cost and more accurate proton beam radiation therapy, which has sparked great scientific interest in the development of image reconstruction from projected data along proton paths that may not necessarily be straight lines through the object to be imaged.

Proton therapy for cancer treatment has gained more recognition and attracted great interest in the past decade as evidenced by the increased number of proton radiation therapy facilities. Different from an X-ray beam, which losses intensity by photon absorption and scatter along the entire beam path of a straight line/strip, a proton loses energy through elastic and inelastic collisions with atomic electrons and nuclei, resulting in a nonlinear path of traversal. This mode of interaction also results in an energy deposition phenomenon known as the Bragg peak in which the proton releases a burst of energy around the end of its trajectory. By this property, protons have the potential to deliver a desired radiation dose to a targeted cancerous volume with minimal harm to the normal tissues.

However, existing proton treatments have several problems associated with radiation dose calculations due to varied positioning of patient anatomy, and are currently performed based on X-ray computed tomography or xCT, with the patient positioned with the help of X-ray radiographs, hence direct visualization of the three-dimensional (3D) patient anatomy in the treatment room is presently impossible, limiting the accuracy of proton therapy. Further, conventional practices for estimating the proton path rely on single line-type curve estimations and fail to consider proton deflection and scattering within the body.

Conventional proton therapy utilizes X-ray beams to produce the computed tomographic images (i.e., xCT) or the X-ray attenuation map of the body for treatment planning. Because of the difference of X-ray and proton interaction with the body tissues, the xCT attenuation map introduces an uncertainty into proton therapy treatment planning. Since the Bragg peak releases a large amount of energy locally, a minor error on the targeted cancerous volume could cause significant harm to the surrounding normal tissues.

Thus, the accuracy of xCT for proton treatment planning is limited due to the difference in physical interactions between X-ray photons and particle protons, which partially obviates the advantage of proton therapy. Further, conventional methods do not accurately modify xCT in the treatment room based on patient position.

Thus, there is a need for more accurate image reconstruction of proton beams to provide improved proton dose distributions and verification of the patient position on the treatment table, and to develop accurate 3D imaging techniques.

SUMMARY OF THE INVENTION

Accordingly, the present invention provides an image reconstruction method for curved paths applicable to heavy particles, in addition to particles following straight line paths. Also provided is a method of use of a proton beam for dose calculation and patient anatomy positioning that provides improved convenience, cost effectiveness and achieves more precise patient treatment.

The present invention also provides improved image reconstruction of particle beams, resulting in improved treatment planning schemes and overcomes the above shortcomings, by minimizing the uncertainty from image reconstruction techniques. The present invention further provides more accurate, efficient reconstruction of pCT images for use in proton therapy and other diagnostic and therapeutic applications.

An aspect of the present invention provides an image reconstruction method including recording projection path information and energy loss information of a plurality of particles traversing an object being imaged, determining an estimated image of the object, based on the projection path information and the energy loss information sampled into a projection format, wherein the estimated image includes an active volume defined by an enclosure border, performing cost function minimization using one of an Adaptive-weighted Total Variation (AwTV) cost function, a Penalized Weighted Least-Squares (PWLS) cost function, and an Alpha-Divergence ($\alpha$-D) cost function, to update the estimated image, performing an iterative updating algorithm corresponding to the cost function, to update the estimated image, and producing a final image based on the estimated image, when a difference between the estimated image and a previously estimated image is lower than a predetermined threshold, with the one of the AwTV cost function, the PWLS cost function, and the $\alpha$-D cost function performed based on the estimated image, the recorded projection path information, the energy loss information and a volumetric path.

BRIEF DESCRIPTION OF THE DRAWINGS

The above and other aspects, features and advantages of certain embodiments of the present invention will be more apparent from the following detailed description taken in conjunction with the accompanying drawings, in which.

DETAILED DESCRIPTION OF EMBODIMENTS OF THE PRESENT INVENTION

Figure 1:
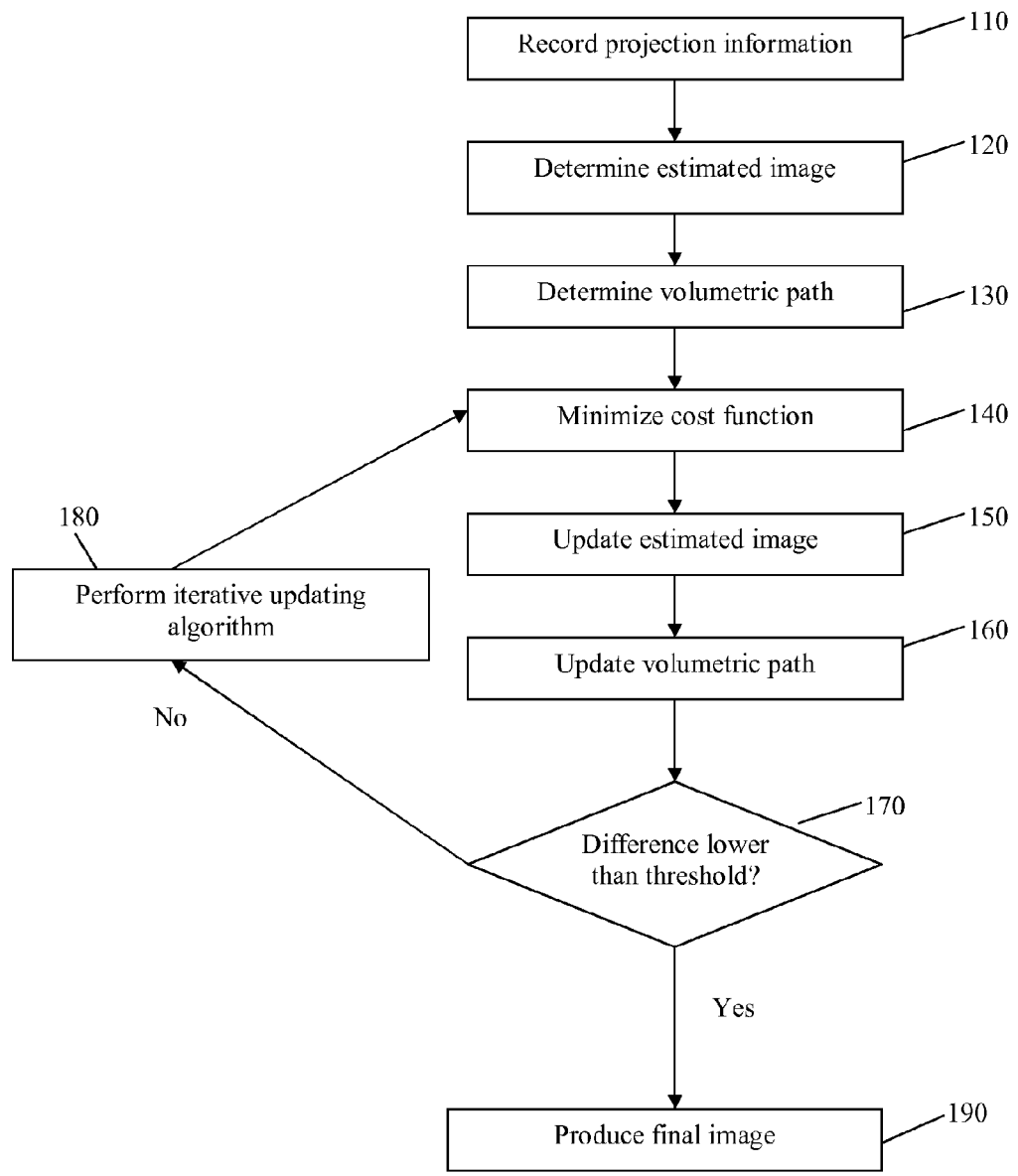
FIG. 1 is a flowchart of image reconstruction by a cost function minimization, according to an embodiment of the present invention.

The following detailed description of various embodiments of the present invention will be made in reference to the accompanying drawings. In describing the present invention, explanation about related functions or constructions known in the art are omitted to avoid obscuring the present invention with unnecessary detail.

The image formation principles of proton beams for pCT rely on hardware configuration and data acquisition to reconstruct an image from projected data along proton trajectories through the body. Image formation for pCT relies on the interaction of incident energy with the tissues inside the body. The knowledge of the interaction and the accuracy of measuring the difference of the exit energy from the incident energy determine the quality of the reconstructed image about the body internals.

A single-proton-tracking pCT scanner tracks individual protons pre and post patient with two-dimensional (2D) sensitive Silicon Strip Detectors (SSDs), providing projection path information, such as proton position and direction at the boundaries of the image space. This projection path information is relied upon in estimating the image, and includes various data for each of the plurality of particles, including energy information, position information, direction information, orientation information and angle information of the plurality of particles, upon entering and exiting the object, object parameter distribution and interaction quantity information. The position of individual protons is determined by individually recording protons with known incident energy by the four planes of position-sensitive silicon detectors which form the scanner reference system. These four planar detectors provide positions as well as azimuth and declination angles of the protons in front and behind the object. US Patent Publication No. 2011/0220794 A1 to Censor et al.

In addition to tracking the position of individual protons, the energy lost by each proton after traversal of the image space is recorded. Using these measurements, an intermediate image is determined, upon a first iteration, by determining the path integral of relative electron density of a known object, for example a water-equivalent object, i.e., an object of water composition but varying electron density that produces the same energy loss as the real object, is determined. Upon subsequent iterations, the integral of relative stopping power along each path is calculated, based on the data obtained from the previous iterations.

When traversing the body, protons lose some of their energy via inelastic collisions with the outer electrons of the tissue atomic components leading to ionizations and excitations. Furthermore, protons are deflected by multiple small-angle scattering from the nuclei of the tissue atomic components, referred to as Multiple Coulomb Scattering (MCS). These two main processes, occurring a great number of times along the macroscopic path length of the protons, lead to the macroscopic effects of the interaction of protons with the tissues inside the body: (1) loss of energy and (2) deflection from their original direction. As individual interaction events occur randomly, these two processes result in a statistical distribution of the following two principal quantities observed for proton imaging: (1) the amount of energy lost by each proton after traversing the body, and (2) the lateral and angular displacements of the proton from its incident position and direction.

According to an aspect of the present invention, the image reconstruction method takes into account that the proton will undergo the MCS process inside the body in a volumetric banana-shaped path to provide interleaved operations of path estimation and image reconstruction.

Referring to FIG. 1, the method begins by recording projection path information and energy loss information of a plurality of particles traversing an object being imaged, in Step 110. An initial image of the object is determined based on the projection path information and energy loss information sampled into a projection sinogram format, in Step 120.

Specifically, measurements are reformed into the projection format producing a sonogram, since measurements of the proton path and energy loss are not recorded in a regular pattern on the detector surface. Thus, the measurements are sampled into a sonogram projection format by arranging the measurements by an interpolation method into a regular data array format on a detector surface. Then, an initial image of the object is determined based on the reformed measurements by Filtered Back-Projection (FBP).

The estimated image includes an active volume defined by an enclosure border of the estimated image. Specifically, from the initial image, the border of the image is determined, and from the border, the entry and exit positions of the proton on the border are determined. The determined positions on the border are used to determine the path within the image volume.

The cost function is performed based on the estimated image, the recorded projection path information, the energy loss information and a volumetric path determined in Step 130.

The cost function minimization is performed in Step 140 using one of an Adaptive-weighted Total Variation (AwTV) cost function, a Penalized Weighted Least-Squares (PWLS) cost function, and an Alpha-Divergence ($\alpha$-D) cost function, to update the estimated image in Step 150.

Figure 6:
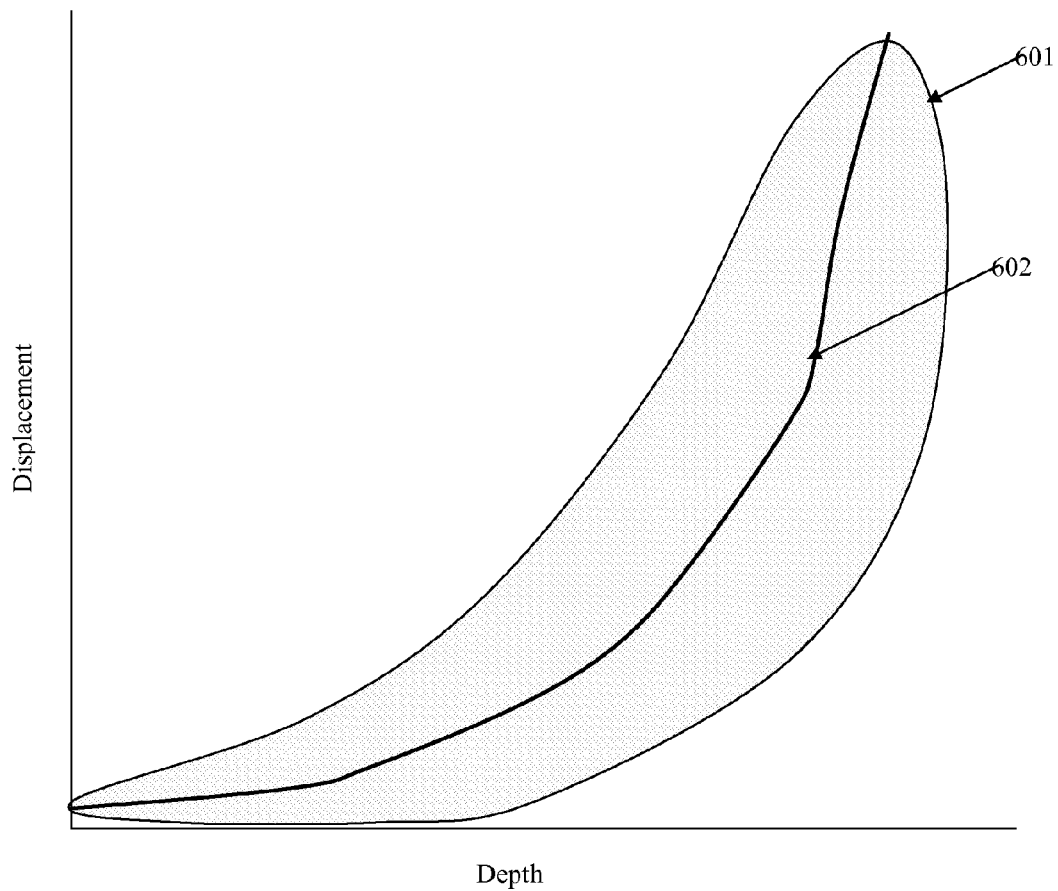
FIG. 6 is a diagram of a volumetric path, according to an embodiment of the present invention.

According to an embodiment of the present invention, the image is reconstructed by taking into account that the proton will undergo the MCS process inside the body, in a volumetric path, as illustrated in FIG. 6. The volumetric path is determined from recorded projection path information and energy loss information, within the active volume.

The volumetric path comprises an object parameter distribution comprising an all path probability distribution in a banana-shaped volume 601 and a centerline 602 of the banana-shaped volume indicates a Most Likely Path (MLP) of the plurality of particles. As illustrated in FIG. 6, the centerline 602 is initially determined when the object is assumed as a uniform medium, such as water, by the use of the recorded projection path information, the energy of the incident proton and the active volume.

A proton has the highest probability traversing through the centerline 602 and lower probabilities of being away from the center. The proton path probability may be described by a Gaussian distribution on a cross section plane, with its standard deviation depending on the medium at that position. Notably, the larger the media difference from the assumed water medium, the larger the standard deviation.

The maximum standard deviation is given by a Cubic Spline Path (CSP) estimated by the use of the recorded projection path information, the energy of incident proton, and the active volume. That is, the difference between the MLP (or the centerline 602) and the CSP on the cross section plane gives the maximum standard deviation of the Gaussian distribution at that position.

An integration is computed along the above estimated volumetric path through the above estimated object image. During integration at a position on the centerline 602, the standard deviation of the Gaussian distribution for that position on the cross section plane is determined by the material at that position. If the position is occupied by water or a less dense material such as fat, air, and other materials less dense than water, then the standard deviation is zero. If the position is occupied by bone, which is considered the densest material in the body, then the standard deviation is given by the difference between the MLP and the CSP at that position. For other materials, the standard deviation is between zero and a maximal value of the difference between the MLP and the CSP. If the standard deviation is not zero, then the highest probability is that the proton passes through the centerline 602 and a lower probability is that the proton passes through other nearby locations near the center within volume 601.

Returning to FIG. 1, the estimated image of the object is determined in Step 120, for example, by sampling the recorded projection path information and energy loss information to create a tomographic projection, reconstructing an initial image by applying FBP image reconstruction using the sampled recorded projection path information and energy loss information, identifying the enclosure border of the initial image and designating a volume within the enclosure border as the active volume of the object being imaged.

The estimated image is updated in Step 150 in iterations by performing an iterative updating algorithm in Step 180 corresponding to the cost function of Step 140, and a final image is produced based on the updated estimated image when a difference between the estimated image and a previously estimated image is determined to be less than a predetermined threshold in Step 170. For example, when the difference between the images is less than 5%, the iterations stop and the final image is output in Step 190.

As discussed above, the iterative updating algorithm for each cost function minimization initially relies on recorded and assumed information, and this information is updated with each iteration. Specifically, an interleaved approach is used, where proton path estimation in Step 160 is interleaved into the iterative process, producing more accurate results.

Upon a first iteration, the volumetric path is estimated based on an estimated path within the initial active volume. The expected data for projection path information and energy loss information is calculated using the estimated volumetric path and the estimated image, in Steps 120 and 130, respectively, and the cost function is performed in Step 140 based on the computed expected data to obtain an updated object image in Step 150. The volumetric path is updated in Step 160 before proceeding to a subsequent iteration, in an interleaved approach of path estimation.

Subsequent iterations provide an updated estimated active volume based on the updated object image resulting in Step 150. The volumetric path is then updated in Step 160, in an interleaved approach, based on the updated volumetric path and the updated object image of previous iterations. The cost function minimization in Step 140 is performed based on updated data, resulting in an updated object image. That is, the cost function is minimized based on updated data, such as the updated active volume, updated volumetric path and updated object image.

The iterations stop when reaching a threshold in Step 170, for example when a difference between a previous estimated object image and the updated estimated object image is greater than a predetermined threshold, for example less than a difference of 5%.

More specifically, an object to be imaged is represented by a three-dimensional (3D) grid of image elements or voxels. In an interleaved approach of iterative image reconstruction, at the beginning or zero iteration, the image at a certain position of the image voxel in the 3D space, is estimated assuming a uniform media at that voxel. Thus, an MLP algorithm is used to perform the projection operation estimating the proton path and providing the expected value of the proton. In subsequent iterations, the difference between the expected value of the proton and the measured value of the proton at a voxel position is then used to update the image. However, after the initial iteration, the medium is determined not to be uniform, and thus the MLP estimation is not a valid estimation of the proton path. A more accurate estimation is determined by simulating the proton path in a non-uniform medium, for example through Monte Carlo simulation. Through this simulation, the difference between the simulated value of the proton and the measured value of the proton at a certain position is then used to update the image estimation at next iteration.

Figure 2:
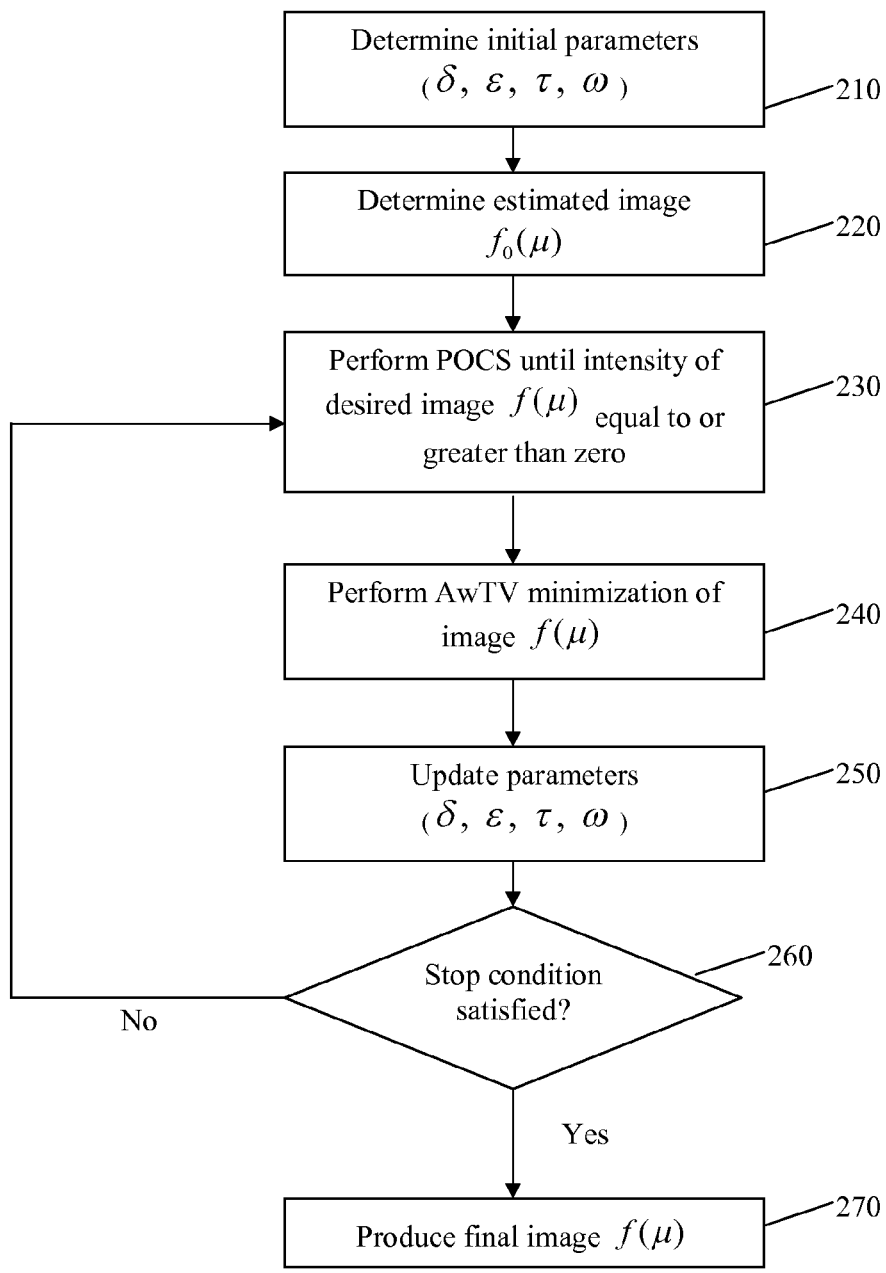
FIG. 2 is a flowchart of image reconstruction by Adaptive-weighted Total Variation (AwTV) minimization, according to an embodiment of the present invention.
Figure 3:
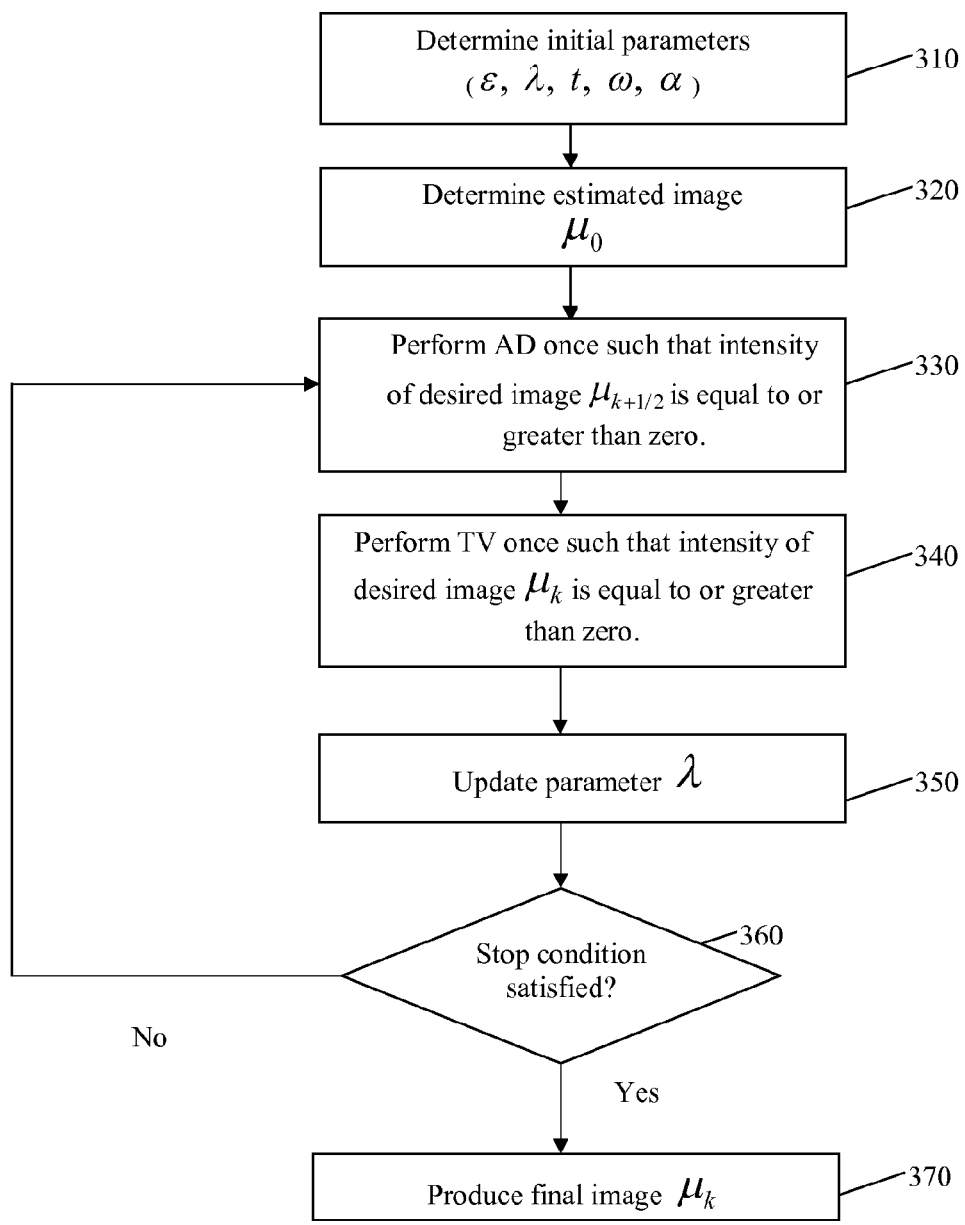
FIG. 3 is a flowchart of image reconstruction by Alpha-Divergence ($\alpha$-D) constrained total variation minimization, according to an embodiment of the present invention.
Figure 4:
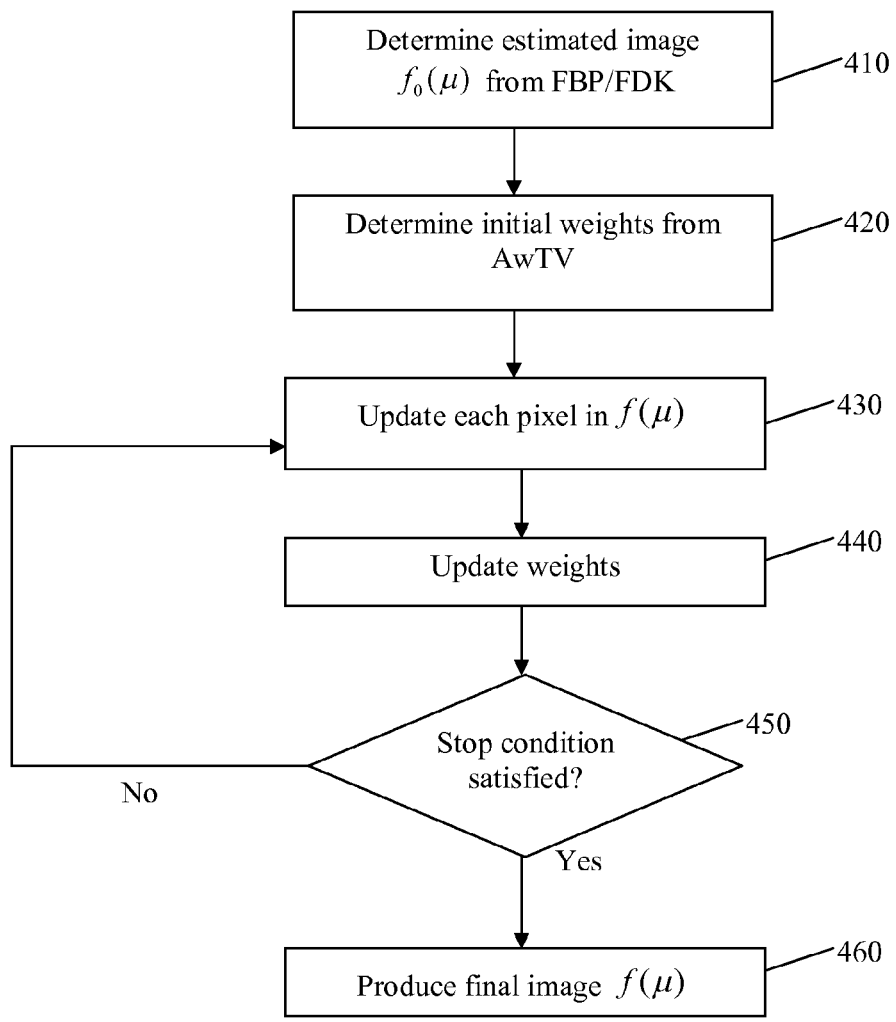
FIG. 4 is a flowchart of image reconstruction by Penalized Weighted Least-Squares (PWLS) minimization, according to an embodiment of the present invention.

Several iterative updating algorithms can be employed in Step 180 to iteratively calculate the solutions to the cost functions in Step 140, including the iterative updating algorithms implemented by a projection onto a Plurality Of Convex Sets (POCS) algorithm for minimizing the AwTV cost function, illustrated FIG. 2, a αD-TV minimizing algorithm for minimizing the α-D cost function, illustrated in FIG. 3 and a Gauss-Seidel (GS) updating algorithm for minimizing the PWLS cost function, as illustrated in FIG. 4.

Referring to FIG. 2, an imaging reconstruction model, according to an embodiment of the present invention, minimizes an AwTV cost function, in Step 240, represented by Equation (1):

$$\min_{\mu \geq 0} \|\eta\|_{AWTV} \qquad (1)$$

The AwTV cost function in Equation (1) is subject to an error tolerance condition $\epsilon$, represented by Equation (2):

$$\|p - H\eta\|_2^2 \leq \epsilon \qquad (2)$$

In Equations (1) and (2), $\eta$ is a vector of the relative electron density distribution (relative to water) within the object to be imaged, p is the recorded energy loss information, and $\epsilon$ is an error tolerance data fidelity constraint determined by a noise level of measurements p, H is an integration operator for computing an expected projection path and energy-loss information, and $H\eta$ is an expected value of a recorded value p expressed as an integral of energy loss along the estimated path through the estimated object image within the estimated active volume at the n-th iteration.

The AwTV cost function is determined by a set of equations, represented as Equation (3):

$$\|\eta\|_{AwTV} = \sum_{i,j} \sqrt{\begin{array}{l}\omega_{i,i-1,j,j}(\eta(i,j)-\eta(i-1,j))^2 + \\ \omega_{i,i,j,j-1}(\eta(i,j)-\eta(i,j-1))^2\end{array}} \quad (3)$$

$$\omega_{i,i-1,j,j} = \exp\left[-\left(\frac{\eta_{i,j}-\eta_{i-1,j}}{\delta}\right)^2\right] \text{ and}$$

$$\omega_{i,i,j,j-1} = \exp\left[-\left(\frac{\eta_{i,j}-\eta_{i,j-1}}{\delta}\right)^2\right]$$

$$\delta \in (4.5616 \times (\eta_{max}-\eta_{min})^2, +\infty).$$

In Equation (3), $\eta$ represents a vector of the relative electron density distribution within the object to be reconstructed, $\eta_{max}$ is a maximum value of the object image and $\eta_{min}$ is a minimum value of the object image, (i, j) represents a position inside the object in 2D representation. Similarly, (i, j, k) can be used to represent a position inside the object in 3D representation.

The image reconstruction model with AwTV minimization is illustrated in FIG. 2 can be applied for sparse data, toward Low-Dose X-ray Computed Tomography (LD-xCT) image reconstruction to mitigate the over-smoothing of edges. The AwTV model is described with reference to Equation (4) as applied to LD-xCT, rewritten from Equations (1) and (2) as follows:

$$\min_{\mu \geq 0} \|\mu\|_{AwTV} \text{ subject to } |p - A\mu| \leq \varepsilon. \quad (4)$$

The AwTV of the to-be-reconstructed image, i.e., $\|\mu\|_{AwTV}$, is defined by a set of equations, represented in Equation (5):

$$\|\mu\|_{AwTV} = \sum_{s,t} \sqrt{\begin{array}{l}w_{s,s-1,t,t}(\mu_{s,t}-\mu_{s-1,t})^2 + \\ w_{s,s,t,t-1}(\mu_{s,t}-\mu_{s,t-1})^2\end{array}}, \quad (5)$$

$$w_{s,s-1,t,t} = \exp\left[-\left(\frac{\mu_{s,t}-\mu_{s-1,t}}{\delta}\right)^2\right] \text{ and}$$

$$w_{s,s,t,t-1} = \exp\left[-\left(\frac{\mu_{s,t}-\mu_{s,t-1}}{\delta}\right)^2\right].$$

In Equations (4) and (5), $\mu$ denotes, for xCT application, the vector of attenuation coefficients of the object with $\mu \in \mathbb{R}^M$, wherein the object is discretized on a 3D grid of M image elements or voxels, s and t are the 2D indices of the location of the attenuation coefficients, p represents the linearized or log-transformed projection data, A is the system matrix which depends on the projection geometry, and its elements are usually modeled as the intersecting lengths of a ray path with the associated voxels on the path. The operator A is similar to H for pCT where H is along a curved path and A is along a straight line.

The form of AwTV in Equation (4) allows for full consideration of the gradient of the desired image and also includes the change of local voxel intensity. Specifically, for a smaller change of voxel intensity, a higher weight will be given, whereas for a larger change of voxel intensity, a weaker weight will be given. Through this diffusion-type weighting coefficients, the intra-region smoothing is encouraged in reference to inter-region smoothing.

Referring to FIG. 2, the image reconstruction algorithm begins by initializing parameters in Step 210 and estimating an image of the object in Step 220.

In Step 210, the algorithm parameters $\delta$, $\epsilon$, $\omega$ and $\tau$ are initialized before the iteration begins. For example, the error tolerance $\epsilon$ is initialized based on the noise level of the data. The selection of the initial value of $\delta$ for the weighted factor in the AwTV depends on the intensity range of the image.

Notably, the parameter $\delta$ of the weight $w_{s,s',t,t'}$ in the AwTV model plays an important role for the AwTV-POCS algorithm due to its effect on the image resolution and noise tradeoff. Based on the tendency of the resolution-noise tradeoff curves, it is possible to obtain an optimal resolution-noise tradeoff in the reconstruction by determining a proper value $\delta$. A minimal value of $\delta$ is determined theoretically as 0.01, which may give the highest resolution. Starting from this minimum value, the value can increase empirically until a proper value $\delta$ is obtained. For example, $\delta$=0.6 generates visually appealing results, and in order to ensure the cost function being convex, let $\delta \in (0.0822, \infty)$.

The initial value of $\omega$ and $\tau$ may be set as 1 and $0.7 \times 10^{-5}$, respectively. Then these initial values may be updated in the iterative process, as shown in Table 1.

In Step 220, the image is estimated, for example by assuming a uniform medium, represented by setting the initial estimate of the image voxel value to 1.

The iterative method in the implementation of the AwTV-POCS algorithm provides an optimization solution in two distinct operations in Steps 230 and 240.

In Step 230, an initially estimated image from Step 220, is updated iteratively by a POCS strategy. In this step, a Simultaneous Algebraic Reconstruction Technique (SART) is used to reconstruct an image from sparse-sampled sinogram data to yield an intermediate estimated image.

In Step 240, the intermediate estimated image is further updated by adopting a gradient descent technique to minimize the AwTV of the intermediate estimated image. To implement the gradient descent technique, the first-order derivative of the AwTV term with respect to each voxel value is calculated.

Specifically, in Step 240, due to the nonlinear form of the AwTV with respect to the image intensity, it is numerically difficult to utilize directly the second-order derivative for the purpose of effectively minimizing the objective function represented by Equation (5).

However, the weights can be pre-computed at current iteration for the AwTV minimization at the next iteration. By this strategy, in Step 240, the gradient descent technique is adapted to minimize the AwTV of the SART-estimated intermediate image where only the first-order derivative of the AwTV term respect to each voxel value is needed, which can be approximately expressed as a set of equations in Equation (6):

$$\frac{\partial \|\mu\|_{AwTV}}{\partial \mu_{s,t}} \approx \frac{2w_{s,s-1,t,t}(\mu_{s,t}-\mu_{s-1,t})+2w_{s,s,t,t-1}(\mu_{s,t}-\mu_{s,t-1})}{\sqrt{\xi+w_{s,s-1,t,t}(\mu_{s,t}-\mu_{s-1,t})^2+w_{s,s,t,t-1}(\mu_{s,t}-\mu_{s,t-1})^2}} + \quad (6)$$

$$\frac{-2w_{s+1,s,t,t}(\mu_{s+1,t}-\mu_{s,t})}{\sqrt{\xi+w_{s+1,s,t,t}(\mu_{s+1,t}-\mu_{s,t})^2+w_{s+1,s+1,t,t-1}(\mu_{s+1,t}-\mu_{s+1,t-1})^2}} +$$

$$\frac{-2w_{s,s,t+1,t}(\mu_{s,t+1}-\mu_{s,t})}{\sqrt{\xi+w_{s,s,t+1,t}(\mu_{s,t+1}-\mu_{s,t})^2+w_{s,s-1,t+1,t+1}(\mu_{s,t+1}-\mu_{s-1,t+1})^2}}$$

In Equation (6), $\xi$ is a relax parameter introduced to avoid the denominator going to zero.

In Step 250, the algorithm parameters are updated iteratively. In Step 260, the condition criteria is checked and when satisfied, the final image is produced in Step 270. If the stop condition is not satisfied in Step 260, Steps 230 through 250 are performed in the next iteration. The stop condition can include a threshold value, for example as described in reference to Step 170 in FIG. 1. The stop condition may also include a predetermined number of general iterations to ensure convergence. Additionally, the stop condition may include a combination of parameters and conditions.

The pseudo code for the AwTV-POCS algorithm is provided in Table 1.

TABLE 1

1: initial : $\mu_{s,t}^{(0)} := 1$; $s = 1, 2, \ldots, S$, $t = 1, 2, \ldots, T$;
2: initial: $\delta, \epsilon, \tau; \omega = 1$;
3: while (stop criterion is not met)
4:   for $j = 1, 2, \ldots, J$; (POCS)
5:     if $j == 1$;
6:       $\mu_{s,t}^{(j)} := SART (\mu_{s,t}^{(0)}, \omega)$;
7:     else $\mu_{s,t}^{(j)} := SART (\mu_{s,t}^{(j-1)}, \omega)$; $s = 1, 2, \ldots, S$, $t = 1, 2, \ldots, T$;
8:     end if
9:   end for
10:   if $\mu_{s,t}^{(J)} > 0$, then $\mu_{s,t}^{(J)} = \mu_{s,t}^{(J)}$; $s = 1, 2, \ldots, S$, $t = 1, 2, \ldots T$;
11:     else $\mu_{s,t}^{(J)} := 0$; $s = 1, 2, \ldots, S$, $t = 1, 2, \ldots, T$;
12:   end if
13:   $dp := \|A \mu_{s,t}^{(J)} - A \mu_{s,t}^{(0)}\|_2$; $s = 1, 2, \ldots, S$, $t = 1, 2, \ldots, T$;
14:   $d \mu_{SART} := \|\mu_{s,t}^{(J)} - \mu_{s,t}^{(0)}\|_2$; $s = 1, 2, \ldots, S$, $t = 1, 2, \ldots, T$;
15:
$$w_{s,s-1,t,t} = \exp\left[\left(\frac{\mu_{s,t}^{(J)} - \mu_{s-1,t}^{(J)}}{\delta}\right)^2\right] \text{ and}$$
$$w_{s,s,t,t-1} = \exp\left[\left(\frac{\mu_{s,t}^{(J)} - \mu_{s,t-1}^{(J)}}{\delta}\right)^2\right];$$
16:   for $k = 1, 2, \ldots, K$; (AwTV gradient descent)
17:
$$\mu_{s,t}^{(J+k)} := \mu_{s,t}^{(J+k-1)} - d \mu_{SART} \cdot \tau \cdot \frac{\nabla \|\mu_{s,t}^{(J+k-1)}\|_{AwTV}}{|\nabla \|\mu_{s,t}^{(J+k-1)}\|_{AwTV}|};$$
18:   end for
19:   if $dp < \epsilon$;
20:     $\omega := 0.995 \times \omega$;
21:   end if
22:   $\mu_{s,t}^{(0)} := \mu_{s,t}^{(J+K)}$;
23:   calculate the criterion;
24:   $\tau = \tau * 0.995$;
25:   end if stop criterion is satisfy In Table 1, the AwTV-POCS is implemented as follows. For an S×T image, each of the I general iteration steps includes performing Step 230 J number of times, i.e., J steps of POCS iterations and K steps of gradient descent iterations in Step 240. The relax parameter $\omega$ in the POCS is decreased and the step-size for the following gradient descend of AwTV is also minimized automatically in the iteration processes. Further, a value of 0.995 is used to update parameters $\omega$ and $\tau$ in lines 20 and 24, to ensure that these two parameters decrease smoothly.

Each outer loop (lines 3-22) is performed by two iteration parts, i.e., the POCS (lines 4-12) in Step 230, and the gradient descent for the AwTV minimization (lines 16-17) in Step 240. The AwTV minimization (lines 16-17) in Step 240 is updated iteratively by the gradient descend procedure. Because the parameter $\omega$ controls the step-size of the POCS (lines 4-12) in Step 230, this algorithm is steepest-descent and based on the values of dp and $d\mu_{SART}$, the adjustable relax parameter $\omega$ is updated at line 20. Additionally, considering the fact that in LD-xCT imaging the linear attenuation coefficient (or in pCT the relative electronic density) of bone is the highest and the linear attenuation coefficient (or the relative electronic density in pCT) of air is the lowest, the maximum $\mu_{max}/\eta_{max}$ and minimum $\mu_{min}/\eta_{min}$ of $\delta$ values can be pre-estimated before image reconstruction.

The AwTV-POCS algorithm described above mitigates oversmoothness on the edges of a resulting image, in a piecewise-smoothed computed tomography (xCT or pCT) image, reconstructed from sparse-sampled data without introducing noticeable artifacts. The AwTV-POCS model considers the anisotropic properties among neighboring voxels in an image. The associated weights in AwTV-POCS are expressed as an exponential function, which can be adaptively adjusted with the local image-intensity gradient to preserve edge details. That is, in order to achieve a reasonable balance between resolution and Contrast-to-Noise Ratio (CNR) in the reconstruction, the associated weights in the AwTV model are expressed as an exponential function, which can be adaptively adjusted with the local image-intensity gradient for preservation of edge details. The AwTV-POCS optimization scheme minimizes the AwTV of the to-be-estimated image subject to data conditions and other constrains for the concerned low-dose xCT and pCT image reconstruction issue and yields images with noticeable gains.

An imaging reconstruction model minimizing an Alpha-Divergence ($\alpha$-D) cost function, according to an embodiment of the present invention, is represented in Equation (7):

$$\Phi(\eta) = D_\alpha(p, q) = \frac{1}{\alpha(1-\alpha)} \int \left[\frac{\alpha p + (1-\alpha)q -}{p^\alpha q^{1-\alpha}}\right] dx + \gamma Q(n), \quad (7)$$

$$\alpha \in (-\infty, +\infty)$$

, with q representing H$\eta$ as an expectation of the measured proton energy loss p, $\eta$ is the relative electron density distribution for pCT, H is the integration operator along the curved proton path inside the object, $\gamma$ is a smoothing parameter which controls a degree of agreement between the estimated and the recorded projection data information, and Q($\eta$) is a penalty term determined by the AwTV cost function.

The methodology for Alpha-Divergence ($\alpha$-D) Constrained Total Variation (TV) minimization as applied for low-dose Computed Tomography (LD-xCT) image reconstruction, is as follows. In order to achieve high-quality low-dose CT image reconstruction, an imaging reconstruction framework with alpha-divergence ($\alpha$-D) constrained total variation ($\alpha$D-TV) minimization, rewritten from Equation (7), is represented in Equation (8):

$$\min_{\mu \geq 0, \mu \in BV(\mathbb{R}^N)} D_\alpha(p, A\mu) + \lambda |\mu|_{BV}. \quad (8)$$

In Equation (8), the subscript BV($\mathbb{R}^N$) denotes the space of functions with bounded total variation in $\mathbb{R}^N$, and $\lambda > 0$ is the global penalty parameter.

As in most image reconstruction algorithms, a cost function consists of two components, a fidelity term and a priori information term. The data fidelity term models the statistics of the measured data. The priori information term regularizes the data fidelity for an optimal solution or image reconstruction.

The data fidelity term in Equation (8), constructed by alpha-divergence measure, is provided by Equation (9):

$$D_\alpha(p, A\mu) = \frac{1}{(1-\alpha)} \sum_{i=1}^{M} [\alpha p_i + (1-\alpha)(A\mu)_i - p_i^\alpha (A\mu)_i^{1-\alpha}] \quad (9)$$

In Equation (9), $\mu = [\mu_1, \mu_2, \ldots, \mu_N]^T \in \mathbb{R}^N$ denotes the attenuation coefficients (for xCT) to be estimated, $p = [p_1, p_2, \ldots, p_M]^T \in \mathbb{R}^M$ represents the linearized or log-transformed projections data (for xCT), and $A = \{A_{i,j}\} \in \mathbb{R}^{M \times N}$ is the system matrix (similar to the H described above for pCT) which depends on the projection geometry, and its elements are modeled as the intersecting lengths of a ray path with the associated voxels on the path.

The priori information term $|\mu|_{BV}$ from Equation (8) is provided by Equation (10):

$$|\mu|_{BV} = \sup_{\omega \in C_0^\infty(\mathbb{R}^N), \|\omega\|_\infty \leq 1} \int_{\mathbb{R}^N} \mu \, div(\omega) \quad (10)$$

In Equation (10), $div(\bullet)$ represents the divergence operator and $\omega$ denotes the dual variable of TV minimization.

Referring to FIG. 3, the image reconstruction algorithm begins by initializing parameters in Step 310 and estimating an image of the object in Step 320, similar to Steps 210 and 220 in FIG. 2.

In Step 310, the initial algorithm parameters are initialized before the iteration begins. For example, the initial values of $\lambda$ and $\omega$ may be set to 1 and $\tau$ to $0.7 \times 10^{-5}$, and error tolerance $\epsilon$ is initialized based on the noise level of the data.

In Steps 330 and 340, the following nested two step optimized scheme is performed, to minimize the $\alpha$D-TV cost function, represented by the set of equations in Equation (11):

$$\mu_{k+1/2}^\alpha(j) = \mu_k^\alpha(j)(\Sigma_i A_{i,j}(p_i/(A\mu)_i)^\alpha)/\Sigma_i A_{i,j},$$

$$\mu_{k+1}^\alpha(j) = \mu_{k+1/2}^\alpha(j) - \alpha \tilde{\lambda}_j \mu_k^\alpha(j) div(\omega_j), \quad (11)$$

where $\tilde{\lambda}_j = \lambda/\Sigma_i A_{i,j}$.

In Step 330, i.e., the first AD step, the iterative form is similar to that of a Maximum Likelihood Expectation-Maximization (ML-EM) algorithm.

In Step 340, the second TV step, a projection gradient descent algorithm is adopted to optimize the dual variable $\omega$, similar to Equation (10). Given an initial dual variable $\omega$, the following update is derived, to achieve an optimal dual parameter $\omega$, in Equation (12):

$$\omega^{n+1} = \frac{\omega^n - t\nabla\left(\alpha\sqrt{2\alpha-1}\tilde{\lambda}\mu_k^\alpha div(\omega) - \frac{\alpha}{\sqrt{2\alpha-1}}\mu_{k+1/2}^\alpha\right)}{1 + t\left|\nabla\left(\alpha\sqrt{2\alpha-1}\tilde{\lambda}\mu_k^\alpha div(\omega) - \frac{\alpha}{\sqrt{2\alpha-1}}\mu_{k+1/2}^\alpha\right)\right|} \quad (12)$$

, with time step t adaptively estimated based on a non-monotone Chambolle projection algorithm for TV image restoration.

Steps 350-370 in FIG. 3 are similar to Steps 250-270 in FIG. 2. That is, in Step 350, the algorithm parameter $\lambda$ is updated iteratively in a smooth fashion, i.e., decreasing slowly. In Step 360, the condition criteria is checked and when satisfied, the final image is produced in Step 370.

The pseudo code for the $\alpha$-D algorithm is provided in Table 2.

TABLE 2

1: initial: $\mu_0(j) := 1; j = 1, 2, \ldots, N$;
2: initial: $\epsilon, \lambda, t, \omega^0, \alpha = 1.3, k = 0, n = 0$;
3: while (stop criterion is not met)
4: $\mu_{k+1/2}^\alpha(j) = \mu_k^\alpha(j)\left(\sum_i A_{i,j}(y_i/(A\mu)_i)^\alpha\right)/$
$\sum_i A_{i,j}; i = 1, 2, \ldots, M; \quad j = 1, 2, \ldots, N$ (AD-step)
5: $\mu_{k+1/2}(j) := \max(\mu_{k+1/2}(j), 0); j = 1, 2, \ldots, N$;
6: $\tilde{\lambda}_j = \lambda / \sum_i A_{i,j}; i = 1, 2, \ldots, M; j = 1, 2, \ldots, N$;
7: $g^n := \nabla\left(\alpha\sqrt{2\alpha-1}\tilde{\lambda}\mu_k^\alpha div(\omega) - \frac{\alpha}{\sqrt{2\alpha-1}}\mu_{k+1/2}^\alpha\right)$;
 (dual variable optimizing)
8: $\omega^{n+1} := \frac{\omega^n - tg^n}{1 + t|g^n|}$; (projection gradient descent)
9: if $\|\omega^{n+1} - \omega^n\| < \epsilon$;
10: $\mu_{k+1}^\alpha(j) = \mu_{k+1/2}^\alpha(j) - \alpha\tilde{\lambda}_j\mu_k^\alpha(j)div(\omega_j); j = 1, 2, \ldots, N$; (TV-step)
11: else go to step 7;
12: endif
13: calculate the criterion;
14: $\lambda := \lambda * 0.995$;
15: $k := k + 1$
16: end if stop criterion is satisfy In Table 2, a value of 0.995 is used to update parameter $\lambda$ in line 14, in the $\alpha$D-TV algorithm to ensure that the parameter decreases smoothly.

The $\alpha$D-TV model for image reconstruction more reasonably measures, by the data fidelity term, the discrepancy between the measured data and the estimated data in the cost function, via the $\alpha$-divergence. Further, to achieve a stable ill-posed image reconstruction, the AwTV penalty, as an edge-preserving prior, is adapted to regularize the solution, i.e., an $\alpha$D-AwTV approach. The $\alpha$D-TV/$\alpha$D-AwTV minimizing algorithms described above perform better in lowering the noise-induced artifacts, while preserving the image edge and accelerating the algorithm convergence speed.

An imaging reconstruction model minimizing a PWLS cost function, according to an embodiment of the present invention, is represented by Equation (13):

$$\Phi(\eta) = (p - H\eta)^T \Sigma^{-1}(p - H\eta) + \gamma Q(\eta), \quad (13)$$

with $H\eta$ being an expectation of the measured proton energy loss p, $\gamma$ is a smoothing parameter which controls a degree of agreement between the estimated and the recorded projection path information, and $\Sigma$ is a diagonal matrix with a diagonal value being a corresponding variance of a data element of p and $Q(\eta)$ is a penalty term determined by the AwTV cost function.

The PWLS-AwTV algorithm method considers the data statistical properties of minimizing data constraints in image reconstruction and is especially advantageous in cases where the data sparsity is not severe and the noise level is relatively high, for example in proton CT where the number of protons is limited while traversing the whole object and low-mAs acquisition for low-dose X-ray CT imaging.

Referring to FIG. 4, the image reconstruction algorithm begins by determining an estimated image in Step 410 and determining initial weights from AwTV in Step 420 by Equation (5) above. Because incident proton orientation will deviate in three dimensions, a cone-beam Feldkamp-Davis-Kress (FDK) algorithm method, which is extended from the FBP method, can be used for imaging a system in cone-beam geometry.

In Step 430, each voxel of the image is updated iteratively by applying the PWLS algorithm described below. In Step 440 the weights of the PWLS algorithm are iteratively updated as well.

In Step 450, similar to the condition steps in the figures described above, the stop condition is checked and when satisfied, the final image is produced in Step 460.

In applying the methodology for low-dose X-ray CT image reconstruction by AwTV-constrained Penalized Weighted Least-Squares (PWLS), two principle sources of causing the CT noise, i.e., the photon counting statistics and the electronic background noise are considered. The measured transmission data I is assumed to statistically follow the Poisson distribution upon a Gaussian distributed background noise, as represented in Equation (14):

$$I = \text{Poisson}(\lambda) + \text{Normal}(m_e, \sigma_e^2), \qquad (14)$$

with $\lambda$ being the mean of Poisson distribution, and $m_e$ and $\sigma_e^2$ as the mean and variance of the Gaussian distribution from the electronic background noise, respectively. The mean $m_e$ of the electronic noise is often calibrated to be zero. Based on this measurement model, a formula of the mean-variance relationship in CT projection domain by considering the effect of the Gaussian distributed electronic background noise at different mAs levels represented by Equation (15):

$$\sigma_{p_i}^2 = \frac{1}{I_{i0}} \exp(p_i) \left( 1 + \frac{\sigma_{e,i}^2 - 1.25}{I_{i0}} \exp(p_i) \right), \qquad (15)$$

In Equation (15), $I_{i0}$ is the mean number of incident photons along projection path i, pt denotes the log-transformed ideal projection datum along path i and is usually called the line integral of the attenuation coefficients along the projection ray, $\sigma_{e,i}^2$ is the variance of the electronic noise associated with the measurement on $p_i$, and $\sigma_{p_i}^2$ represents the estimated variance of measuring projection datum $p_i$.

For CT image reconstruction, the associated cost function of penalized weighted least-squares (PWLS) in Equation (13) is rewritten as Equation (16):

$$\Phi(\mu) = (p - A\mu)^T \Sigma^{-1} (p - A\mu) + \beta R(\mu). \qquad (16)$$

In Equation (16), p is the acquired projection data and A represents the system transfer matrix, which depends on the projection geometry, and its elements of $\alpha_{i,j}$ can be calculated as the length of the intersection of projection ray i with voxel j, $\mu$ is the vector of ideal attenuation coefficients to be reconstructed.

The first term on the right hand side is the data fidelity term described as a weighted least-squares (WLS) measurement wherein the matrix $\Sigma$ is a diagonal matrix and its i-th element denotes the variance of the projection datum at detector i.

The second term on the right hand side is the priori penalty term. The AwTV is used as the penalty term, represented by the set of equations in Equation (17):

$$\|\mu\|_{AwTV-3D} = \sum_{s,t,z} \begin{bmatrix} w_{s,s-1,t,t,z,z}(\mu_{s,t,z} - \mu_{s-1,t,z})^2 + \\ w_{s,s,t,t,z,z-1}(\mu_{s,t,z} - \mu_{s,t,z-1})^2 + \\ w_{s,s,t,t-1,z,z}(\mu_{s,t,z} - \mu_{s,t-1,z})^2 \end{bmatrix}^{\frac{1}{2}} \qquad (17)$$

-continued $$w_{s,s-1,t,t,z,z} = \exp\left[-\left(\frac{\mu_{s,t,z} - \mu_{s-1,t,z}}{\delta}\right)^2\right],$$

$$w_{s,s,t,t-1,z,z} = \exp\left[-\left(\frac{\mu_{s,t,z} - \mu_{s,t-1,z}}{\delta}\right)^2\right]$$

and $$w_{s,s,t,t,z,z-1} = \exp\left[-\left(\frac{\mu_{s,t,z} - \mu_{s,t,z-1}}{\delta}\right)^2\right]$$

In Equation (17), s and t are the 2D indices of the location of the attenuation coefficients along in-plane domain (slice), z is the indices of the attenuation coefficients along axial direction, $\delta$ in the weights is a scale factor which controls the strength of the diffusion during each iteration.

The pseudo code for the PWLS algorithm is provided in Table 3.

TABLE 3

1: Initialization:
2: $\hat{\mu} = \text{FDK}\{\hat{p}\};$
3: $\hat{r} = \hat{p} - A\hat{\mu};$
4: $s_j = a'_j \Sigma^{-1} a_j, \forall j;$
5: $$w_{jm} = \exp\left[-\left(\frac{\mu_j - \mu_m}{\delta}\right)^2\right], m \in N_j;$$
6: For each iteration:
7:   For each pixel j = {s, t, z}:
8:     For each neighbor m ∈ $N_j$
9:     if m ∈ M = {s − 1,t,z}∪{s,t − 1,z}∪{s,t,z − 1}
10: $$w'_{jm} := \frac{w_{jm}}{\sqrt{\sum_{m \in M} w_{jm}(\mu_j - \mu_m)^2 + \varepsilon}};$$
11: if m = {s + 1, t, z},
12: $$w'_{jm} := \frac{w_{jm}}{\sqrt{\begin{array}{l} w_{s,s+1,t,t,z,z}(\mu_{s+1,t,z} - \mu_j) + \\ w_{s+1,s+1,t,t-1,z,z}(\mu_{s+1,t,z} - \mu_{s+1,t-1,z}) + \\ w_{s+1,s+1,t,t,z,z-1}(\mu_{s+1,t,z} - \mu_{s+1,t,z-1}) + \varepsilon \end{array}}};$$
13: else if m = {s, t + 1, z},
14: $$w'_{jm} := \frac{w_{jm}}{\sqrt{\begin{array}{l} w_{s,s,t+1,t,z,z}(\mu_{s,t+1,z} - \mu_j) + \\ w_{s,s-1,t+1,t+1,z,z}(\mu_{s,t+1,z} - \mu_{s-1,t+1,z}) + \\ w_{s,s,t+1,t+1,z,z-1}(\mu_{s,t+1,z} - \mu_{s,t+1,z-1}) + \varepsilon \end{array}}};$$
15: else if m = {s, t, z + 1},
16: $$w'_{jm} := \frac{w_{jm}}{\sqrt{\begin{array}{l} w_{s,s,t,t,z+1,z}(\mu_{s,t,z+1} - \mu_j) + \\ w_{s,s-1,t,t,z+1,z+1}(\mu_{s,t,z+1} - \mu_{s-1,t,z+1}) + \\ w_{s,s,t-1,t,z+1,z+1}(\mu_{s,t,z+1} - \mu_{s,t-1,z+1}) + \varepsilon \end{array}}};$$
17: end if
18: $\hat{\mu}_j^{old} := \hat{\mu}_j;$
19: $$\hat{\mu}_j^{new} := \frac{a'_j \Sigma^{-1} \hat{r} + s_j \hat{\mu}_j^{old} + \beta \sum_{m \in N_j} w'_{jm} \hat{\mu}_m^{old}}{s_j + \beta \sum_{m \in N_j} w'_{jm}};$$

TABLE 3-continued

```
20:        μ̂_j := max {0, μ̂_j^new};
21:        r̂ := r̂ + a_j (μ_j^old − μ_j);
22:      end for
23:   end for
24:
      update w'_{jm} = exp[−((μ_j − μ_m)/δ)^2], m ∈ N_j;
25:   end if stop criterion is satisfied.
```

Since the weights in AwTV depend on the local intensity of the image, implementation of the second-order derivative of the AwTV term in the above PWLS algorithm is complicated. The optimization of the cost function is in two separate steps. The first step is using the separable paraboloid surrogate method and the second step is using the gradient descent method to minimize the AwTV-related term. By executing these two steps iteratively, a desired image can be obtained. These iteration steps are summarized in Table 4, with a constant of 1.25 in Equation (15) above.

TABLE 4

```
1    Initialization:
2      μ̂ = FBP {p̂};
3      p = Aμ;
4
       Σ = diag{σ_{p_i}^2} = diag{ (1/I_{i0}) exp(p̂_i)(1 + (1/I_{i0}) exp(p̂_i)(σ_{e,i}^2 − 1.25))};

5    For each iteration:
6      Step 1: Minimize first term (p̂ − Aμ)^T Σ^{-1} (p̂ − Aμ) by 7
                              M Σ_{i∈S} a_{i,j} (1/σ_{p_i}^2) ([Aμ̂]_i − p̂_i)
       μ̂_j|_{new} = μ̂_j|_{old} − ─────────────────────────────────────────
                              Σ_{i∈S} ( a_{i,j} (1/σ_{p_i}^2) Σ_{j=1}^N a_{i,j} )  |_{μ=μ_old}

8      μ̂_j|_{new} = argmax {μ̂_j|_{new}, 0};
9      p̂|_{new} = A μ|_{new};
10     Step 2: AwTV gradient descent
11     μ̂_j|_{new+1} = gradient descent(μ̂_j|_{new})
12     p̂|_{new+1} = A μ|_{new+1}
13     update Σ using p̂|_{new+1};
14   End
```

The PWLS strategy, employing the PWLS-AwTV algorithm as described above, mitigates the noise effect and produces a higher quality image. The PWLS strategy can be implemented by using the PWLS-AwTV algorithm and is especially advantageous in cases of sufficient angular sampling and low-dose on respective views.

An imaging reconstruction model, according to an embodiment of the present invention, minimizes an AwTV cost function, expanded to a TV-Stroke cost function represented by Equation (18):

$$n = \nabla f(\eta) = \left(\frac{\partial f(\eta)}{\partial \eta_x}, \frac{\partial f(\eta)}{\partial \eta_y}\right)^T \text{ and} \tag{18}$$

$$\tau = \nabla^\perp f(\eta) = \left(\frac{\partial f(\eta)}{\partial \eta_y}, -\frac{\partial f(\eta)}{\partial \eta_x}\right)^T.$$

In Equation (18), $\nabla$ is a vector differential operator, T is a transpose operator, and $\nabla^\perp$ is an orthogonal vector differential operator, wherein $\nabla$ satisfies an irrotationality condition, $\nabla^\perp$ satisfies an incompressibility condition, $\eta$ is the relative electron density distribution for pCT, $f$ is a function of $\eta$, n is a normal vector, and $\tau$ is a tangential vector.

Specifically, in the methodology for TV-Stokes strategies for xCT image reconstruction, given a 2D image $f(\mu)$ (also in 3D space), where $\mu$ is the attenuation coefficient in xCT image reconstruction field, two orthogonal vectors, the normal vector n and the tangential vector $\tau$ of the image are defined by Equation (19):

$$n = \nabla f(\mu) = \left(\frac{\partial f(\mu)}{\partial \mu_x}, \frac{\partial f(\mu)}{\partial \mu_y}\right)^T \text{ and} \tag{19}$$

$$\tau = \nabla^\perp f(\mu) = \left(\frac{\partial f(\mu)}{\partial \mu_y}, -\frac{\partial f(\mu)}{\partial \mu_x}\right)^T,$$

with $\nabla$ being a vector differential operator, T representing the transpose operator, and $\nabla^\perp$ being an orthogonal vector differential operator.

These two vector fields should satisfy the irrotationality condition and incompressibility condition separately. The irrotationality condition and incompressibility condition can be mathematically expressed by Equation (20):

$$\nabla \times n = 0 \text{ and } \nabla \cdot \tau = 0, \tag{20}$$

with the left side being the cross product and a mathematical description of the irrotationality condition, and the right side being the dot product and a mathematical description of the incompressibility condition.

Total Variation Stokes (TVS) strategy requires the desired image satisfy the incompressibility condition in the tangential vector field and data fidelity. The desired image is reconstructed by the following optimization problem, represented by Equation (21):

$$\min_{\tau,\mu} \int_\Omega |\nabla \tau| d\mu + \int_\Omega \left(|\nabla f| - \nabla f \cdot \frac{n}{|n|}\right) d\mu \tag{21}$$

subject to $\nabla \cdot \tau = 0$, $\|P - A\mu\|_2^2 \le \sigma^2$.

In Equation (21) p is the projection data, A is the transfer matrix or system matrix, which is related to the projection geometry of the CT scanner, $\sigma$ is the error tolerance between the projection data and the projections of the to-be-estimated image. The optimization problem in Equation (21) is solved with multiple variables by decomposing the objective function to two sub-optimization problems, as described with reference to FIG. 5.

Figure 5:
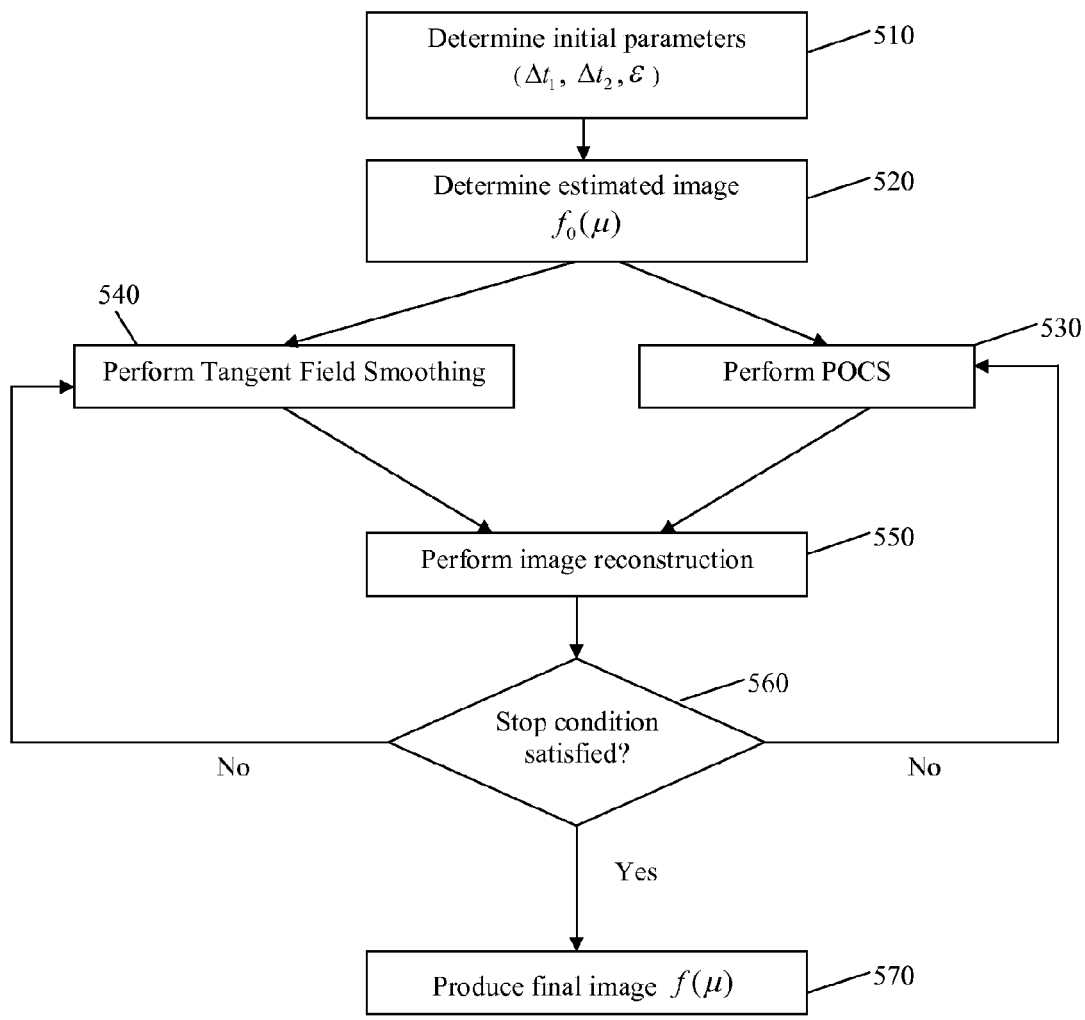
FIG. 5 is a flowchart of an image reconstruction method by TV-Stokes minimization, according to an embodiment of the present invention.

Referring to FIG. 5, the initial parameters are determined in Step 510 and an initial image is estimated in Step 520.

In Step 540, the normal vector is estimated with incompressibility constraints, in the Tangent Field Smoothing (TFS) operation. The minimization problem of Step 540 is represented by Equation (22):

$$\min_\tau \int_\Omega |\nabla \tau| d\mu \text{ subject to } \nabla \cdot \tau = 0. \tag{22}$$

In Step 550, the desired image is reconstructed by fitting it to the estimated normal field with constraints from data fidelity, obtained by solving the following minimization Equation (23):

$$\min_\mu \int_\Omega \left(|\nabla f| - \nabla f \cdot \frac{n}{|n|}\right) d\mu \text{ subject to } \|P - A\mu\|_2^2 \leq \sigma^2. \tag{23}$$

In Step 530, $\|P-A\mu\|_2^2 \leq \sigma^2$ is solved by performing the POCS strategy described above. Thus, the desired image can be obtained in Step 570, by executing Steps 540 and 550 iteratively until a stop condition is satisfied in Step 560.

More specifically, the two-step algorithm for TVS strategy is described as performed in two distinct operations, by applying Tangent Field Smoothing (TFS) and performing image reconstruction. The TFS operation in Step 540 is provided by Equation (24):

$$\mathcal{L}(\tau, \lambda) = \int_\Omega |\nabla \tau| d\mu + \lambda \int_\Omega \nabla \cdot \tau d\mu + \frac{\beta}{2} \int_\Omega (\nabla \cdot \tau)^2 d\mu, \tag{24}$$

where $\lambda$ is the Lagrange multiplier and $\beta$ is a penalty parameter. The saddle point of this optimization problem is the following set of Euler-Lagrange Equations (25)-(27):

$$-\nabla \cdot \left(\frac{\nabla \tau}{|\nabla \tau|}\right) - \nabla \lambda - \beta \nabla (\nabla \cdot \tau) = 0 \text{ in } \Omega, \tag{25}$$

$$\nabla \cdot \tau = 0 \text{ in } \Omega, \tag{26}$$

with the Neumann boundary condition, $$\left(\frac{\nabla \tau}{|\nabla \tau|} + \lambda I\right) \cdot v = 0 \text{ on } \partial \Omega, \tag{27}$$

where $v$ is the unit outward normal and $I$ is the identity matrix. To solve such minimization problem, we use the method of gradient-descent method by considering an artificial time variable t, utilizing Equations (28)-(29):

$$\frac{\partial \tau}{\partial t} - \nabla \cdot \left(\frac{\nabla \tau}{|\nabla \tau|}\right) - \nabla \lambda - \beta \nabla (\nabla \cdot \tau) = 0 \text{ in } \Omega, \tag{28}$$

$$\frac{\partial \lambda}{\partial t} \nabla \cdot \tau = 0 \text{ in } \Omega. \tag{29}$$

The image reconstruction operation in Step 550 is provided by Equations (30)-(33). Specifically, after tangential vector $\tau^*$ is smoothed in Step 540, of the above TFS algorithm by solving Equations (28) and (29), the optimized normal vector $n^*$ can be found, which will be used to reconstruct the low-dose CT image by fitting the normal vector of the desired image with the optimized normal vector $n^*$ with constraints from the fidelity of the acquired projection data as described in Equation (23). However, these two terms require integration in different domains, the image domain and the projection domain. Thus, due to the difficulty of solving this problem simultaneously, by using the simple AL method below, these two terms are solved separately.

The first term is solved by using Euler-Lagrange (EL) method, represented by Equation (30):

$$\mathcal{L}(f, \alpha) = \int_\Omega \left(|\nabla f| - \nabla f \cdot \frac{n}{|n|}\right) d\mu, \tag{30}$$

The corresponding set of EL equations for the saddle point is represented in Equations (31)-(32):

$$\nabla \cdot \left(\frac{\nabla f}{|\nabla f|} - \frac{n}{|n|}\right) = 0, \text{ in } \Omega, \tag{31}$$

with the Neumann boundary condition:

$$\left(\frac{\nabla f}{|\nabla f|} - \frac{n}{|n|}\right) \cdot \vec{\gamma} = 0, \text{ on } \delta\Omega, \tag{32}$$

where $\vec{\gamma}$ represents outwards unit normal vectors on the boundary $\partial\Omega$.

The fidelity term is solved by performing the POCS algorithm in Step 530, represented by Equation (33):

$$\|P-A\mu\|_2^2 \leq \sigma^2. \tag{33}$$

Thus the desired image solution of Equation (23) can be obtained iteratively by using Equations (32) and (33).

In implementing the updating function for the first TFS operation in Step 540, several assumptions are made:

1. Assume the forward/backward difference operators along x and y axes are $D_x^{\pm}$ and $D_y^{\pm}$.
2. Assume the centered difference operators along x and y axes are $C_x^h$ and $C_y^h$, where h corresponds to the order of neighbors of the central pixels.
3. Define a vector (u,v) as:

$$\tau = \nabla^+ f(\mu) = \left(\frac{\partial f}{\partial \mu_y}, -\frac{\partial f}{\partial \mu_x}\right)^T = (u, v)^T \tag{34}$$

The value of the variable u, v and $\lambda$ at step n+1 can be calculated by Equations (35)-(41):

$$v^{n+1} = v^n + \Delta t_2 \left( \begin{array}{l} D_x^-\left(\frac{D_x^+ v^n}{T_1^n}\right) + \\ D_y^-\left(\frac{D_y^+ v^n}{T_2^n}\right) + D_x^-(\lambda^n + Div(\tau^n)) \end{array} \right), \tag{35}$$

$$u^{n+1} = u^n + \Delta t_2 \left( \begin{array}{l} D_x^-\left(\frac{D_x^+ u^n}{T_2^n}\right) + \\ D_y^-\left(\frac{D_y^+ u^n}{T_1^n}\right) + D_y^-(\lambda^n + Div(\tau^n)) \end{array} \right), \tag{36}$$

$$\lambda^{n+1} = \lambda^n + \Delta t_2 (D_x^+ v^n + D_y^+ u^n), \tag{37}$$

where $$Div(\tau^n) = D_x^+ v^n + D_y^+ u^n, \tag{38}$$

$$T_1 = \sqrt{(A_x(C_y^h v^n))^2 + (D_x^+ v^n)^2 + (D_y^+ u^n)^2 + (M_y(C_x^h u^n))^2 + \varepsilon}, \tag{39}$$

$$T_2 = \sqrt{(A_y(C_x^h v^n))^2 + (D_y^+ v^n)^2 + (D_x^+ u^n)^2 + (M_x(C_y^h u^n))^2 + \varepsilon}, \tag{40}$$

-continued $$M_x w = (w(x, y) + w(x+h, y))/2 \quad (41)$$
and
$$M_y w = (w(x, y) + w(x, y+h))/2.$$

The updating function for the second operation in Step 550 is solved by Equations (42)-(45) as follows. From Equation (38) we know that $$n = \nabla f(\mu) = \left(\frac{\partial f}{\partial \mu_x}, \frac{\partial f}{\partial \mu_y}\right)^T = (u, v),$$

utilizing Equations (42)-(45):

$$\mu^{n+1} = \mu^n + \Delta t_2\left(D_x^-\left(\frac{D_x^+ f^n}{T_3^n} - n_1\right) + D_y^-\left(\frac{D_y^- f^n}{T_4^n} - n_2\right)\right), \quad (42)$$

where $$T_3 = \sqrt{D_x^+ f^n + (M_x(C_y^h f^n))^2 + \varepsilon}, \quad (43)$$

$$T_4 = \sqrt{D_y^+ f^n + (M_y(C_x^h f^n))^2 + \varepsilon}, \quad (44)$$

$$n_1 = \frac{u}{\sqrt{u^2 + (M_x(M_y v))^2 + \varepsilon}} \text{ and} \quad (45)$$

$$n_2 = \frac{v}{\sqrt{v^2 + (M_y(M_x u))^2 + \varepsilon}}$$

The updating function for Step 2 uses the PCOS algorithm in Step 530, as described above.

The TV-Stokes strategies for CT image reconstruction in the AwTV-POCS algorithm are described in the pseudo code in Table 5.

TABLE 5

```
1:   initial: μ^(0) := FBP;
2:   initial: t1, t2 and ε
3:   calculate the initial vectors u and v from μ^(0);
3:   while stop criterion is not met
4:       for n = 1,2, . . . , N; (TFS)
5:           calculate calculate τ^n, T_1^n, T_2^n;
```

$$v^{n+1} = v^n + \Delta t_2\left(D_x^-\left(\frac{D_x^+ v^n}{T_1^n}\right) + D_y^-\left(\frac{D_y^+ v^n}{T_2^n}\right) + D_x^-(\lambda^n + \text{Div}(\tau^n))\right),$$

$$u^{n+1} = u^n + \Delta t_2\left(D_x^-\left(\frac{D_x^+ u^n}{T_2^n}\right) + D_y^-\left(\frac{D_y^+ u^n}{T_1^n}\right) + D_y^-(\lambda^n + \text{Div}(\tau^n))\right),$$

```
         λ^(n+1) = λ^n + Δt_2 (D_x^+ v^n + D_y^+ u^n),
6:       end for
7:       for j = 1, 2, . . . , J; (POCS)
8:           if j = 1; =
9:               μ^(j) := SART (μ^(0), ω);
10:          else μ^(j) := SART(μ^(j-1), ω);
11:          end if
12:      end for
13:      if μ_{x,y}^(J) > 0, then μ_{x,y}^(J) = μ_{x,y}^(J); x = 1, 2, . . . X, y = 1, 2, . . . ,Y;
14:          else μ_{x,y}^(J) := 0; x = 1, 2, . . . , X, y = 1, 2, . . . ,Y;
15:      end if
16:      for i = 1, 2, . . . , I; (IR)
17:          calculate n_1, n_2, T_3^i, T_4^i;
```

TABLE 5-continued

```
18:
```

$$\mu^{i+1} = \mu^i + \Delta t_2\left(D_x^-\left(\frac{D_x^+ \mu^i}{T_3^i} - n_1\right) + D_y^-\left(\frac{D_y^+ \mu^i}{T_4^i} - n_2\right)\right),$$

```
         x = 1, 2, . . . , X, y = 1, 2, . . . , Y;
19:      end for
20:  end if stop criterion is satisfy
```

While the present invention has been shown and described with reference to various embodiments of the present invention thereof, it will be understood by those skilled in the art that changes in form and details may be made therein without departing from the spirit and scope of the present invention as defined by the appended claims and equivalents thereof.

What is claimed is:

1. A method for imaging an object, the method comprising:
   recording projection path information and energy loss information of a plurality of particles traversing an object;
   determining an estimated image based on the projection path information and the energy loss information sampled into a projection format, wherein the estimated image includes an active volume defined by an enclosure border;
   updating the estimated image by performing cost function minimization using one of an Adaptive-weighted Total Variation (AwTV) cost function, a Penalized Weighted Least-Squares (PWLS) cost function, and an Alpha-Divergence (α-D) cost function;
   updating the estimated image by performing an iterative updating algorithm corresponding to the cost function minimization; and
   when a difference between the updated estimated image and a previously estimated image is lower than a predetermined threshold, producing a final image based on the estimated image,
   wherein the one of the AwTV cost function, the PWLS cost function, and the α-D cost function is performed based on the estimated image, the recorded projection path information and energy loss information and a volumetric path.

2. The method of claim 1, wherein the step of determining the estimated image comprises:
   sampling the recorded projection path information and energy loss information to create a tomographic projection;
   reconstructing an initial image by applying a Filtered Back-Projection (FBP) image reconstruction method using the sampled recorded projection path information and energy loss information;
   identifying the enclosure border of the initial image; and
   designating a volume within the enclosure border as the active volume of the object being imaged.

3. The method of claim 1, wherein the step of performing the iterative updating algorithm corresponding to the cost function minimization comprises:
   performing a first iteration by updating the volumetric path based on an estimated path within the active volume, computing expected data for projection path information and energy loss information using the updated volumetric path and the estimated image, performing the cost function based on computed expected data and recorded data, and obtaining an updated object image; and
   performing subsequent iterations by updating the estimated active volume based on the updated object image, updating the volumetric path based on the updated active volume and the updated object image, minimizing the cost function based on the updated active volume, updated volumetric path, updated object image, the computed expected data and the recorded data, to further update the object image.

4. The method of claim 1, wherein the projection path information includes energy loss information of each of the plurality of particles, position information, direction information, orientation information, and angle information of the plurality of particles, upon entering and exiting the object, object parameter distribution and interaction quantity information.

5. The method of claim 1, wherein the volumetric path is a banana-shaped volume determined from recorded projection path information and energy loss information within the active volume,
wherein the banana-shaped volume provides an object parameter distribution including an all path probability distribution, and
wherein a centerline of the banana-shaped volume indicates a most likely path of the plurality of particles.

6. The method of claim 1, wherein the iterative updating algorithm comprises one of:
a projection onto a Plurality Of Convex Sets (POCS) algorithm for minimizing the AwTV cost function;
a Gauss-Seidel (GS) updating algorithm for minimizing the PWLS cost function; and
an αD-TV minimizing algorithm for minimizing the α-D cost function.

7. The method of claim 1, wherein the AwTV cost function is determined by:

$$\min_{\eta \geq 0} \|\eta\|_{AwTV},$$

wherein the AwTV cost function is subject to an error tolerance condition $\epsilon$, represented by:

$$\|p - H\eta\|_2^2 \leq \epsilon, \text{and}$$

wherein $\eta$ is a vector of a relative electron density distribution within the object, p is the recorded energy loss information, and $\epsilon$ is an error tolerance data fidelity constraint determined by a noise level of p, H is an integration operator for computing an expected energy-loss information along a projection path, and $H\eta$ is an expected value of a recorded value p expressed as an integral of energy loss along the estimated path through the estimated object image within the estimated active volume at the n-th iteration.

8. The method of claim 7, wherein the AwTV cost function is determined by:

$$\|\eta\|_{AwTV} = \sum_{i,j} \sqrt{\omega_{i,i-1,j,j}(\eta(i,j) - \eta(i-1,j))^2 + \omega_{i,i,j,j-1}(\eta(i,j) - \eta(i,j-1))^2}$$

$$\omega_{i,i-1,j,j} = \exp\left[-\left(\frac{\eta_{i,j} - \eta_{i-1,j}}{\delta}\right)^2\right] \text{ and}$$

-continued $$\omega_{i,i,j,j-1} = \exp\left[-\left(\frac{\eta_{i,j} - \eta_{i,j-1}}{\delta}\right)^2\right]$$

$$\delta \in (4.5616 \times (\eta_{max} - \eta_{min})^2, +\infty),$$

wherein, $\eta$ represents a vector of the relative electron density distribution within the object, $\eta_{max}$ is a maximum value of the object image and $\eta_{min}$ is a minimum value of the object image, and (i,j) represents a position inside the object in two-dimensional representation.

9. The method of claim 1, wherein the AwTV cost function is expanded to a TV-Stroke cost function represented by:

$$n = \nabla f(\eta) = \left(\frac{\partial f(\eta)}{\partial \eta_x}, \frac{\partial f(\eta)}{\partial \eta_y}\right)^T \text{ and}$$

$$\tau = \nabla^\perp f(\eta) = \left(\frac{\partial f(\eta)}{\partial \eta_y}, -\frac{\partial f(\eta)}{\partial \eta_x}\right)^T,$$

where $\nabla$ is a vector differential operator, T is a transpose operator, and $\nabla^\perp$ is an orthogonal vector differential operator, wherein $\nabla$ satisfies an irrotationality condition, $\nabla^\perp$ satisfies an incompressibility condition, $\eta$ represents a vector of the relative electron density distribution within the object to be reconstructed, $f(\eta)$ is a function of $\eta$, n is a normal vector, and $\tau$ is a tangential vector.

10. The method of claim 1, wherein the α-D cost function is represented by:

$$\Phi(\eta) = D_\alpha(p,q) = \frac{1}{\alpha(1-\alpha)} \int [\alpha p + (1-\alpha)q - p^\alpha q^{1-\alpha}] dx + \gamma Q(\eta),$$

$$\alpha \in (-\infty, +\infty)$$

where q represents $H\eta$ and is an expectation of the measured proton energy loss p, $\gamma$ is a smoothing parameter which controls a degree of agreement between the estimated and the recorded projection path information, and $Q(\eta)$ is a penalty term solved by the AwTV cost function.

11. The method of claim 1, wherein the PWLS cost function is represented by:

$$\Phi(\eta) = (p - H\eta)^T \Sigma^{-1}(p - H\eta) + \gamma Q(\eta),$$

wherein $H\eta$ is an expectation of the measured proton energy loss p, $\gamma$ is a smoothing parameter which controls a degree of agreement between the estimated and the recorded projection path information, $\Sigma$ is a diagonal matrix with a diagonal value being a corresponding variance of a data element of p, and $Q(\eta)$ is a penalty term solved by the AwTV cost function.

12. The method of claim 1, wherein the particles traversing the object are one of protons, neutrons, muons, carbon and alpha particles.

13. The method of claim 1, wherein the plurality of particles includes X-ray photons, Gamma-ray photons, and wherein the recorded projection path is a straight line.

* * * * *